United States Patent
Balkus, Jr. et al.

(10) Patent No.: US 6,790,672 B2
(45) Date of Patent: Sep. 14, 2004

(54) ENCODED MOLECULAR SIEVE PARTICLE-BASED SENSORS

(75) Inventors: Kenneth J. Balkus, Jr., The Colony, TX (US); Paul Pantano, Plano, TX (US); Claudia C. Meek, Dallas, TX (US); Decio H. Coutinho, Dallas, TX (US)

(73) Assignee: Board of Regents the University of Texas System, Austin, TX (US)

( * ) Notice: Subject to any disclaimer, the term of this patent is extended or adjusted under 35 U.S.C. 154(b) by 430 days.

(21) Appl. No.: 10/079,635

(22) Filed: Feb. 19, 2002

(65) Prior Publication Data

US 2004/0013569 A1 Jan. 22, 2004

Related U.S. Application Data

(60) Provisional application No. 60/269,909, filed on Feb. 19, 2001.

(51) Int. Cl.[7] ............................................. G01N 21/64
(52) U.S. Cl. .................................... 436/172; 422/82.07
(58) Field of Search ................ 385/141, 12; 422/82.05, 422/82.08, 82.11; 436/164, 172

(56) References Cited

U.S. PATENT DOCUMENTS

| 5,028,545 | A | * | 7/1991 | Soini ........................... 436/501 |
| 5,149,661 | A | * | 9/1992 | Gjerde et al. ................ 436/178 |
| 5,244,636 | A | | 9/1993 | Walt et al. ................ 422/82.07 |
| 5,250,264 | A | | 10/1993 | Walt et al. ................ 422/82.07 |
| 5,529,686 | A | * | 6/1996 | Hagen et al. ............. 210/198.2 |
| 5,565,324 | A | * | 10/1996 | Still et al. ........................ 435/6 |
| 5,593,843 | A | * | 1/1997 | Malick et al. ................ 435/7.1 |
| 5,719,322 | A | * | 2/1998 | Lansbarkis et al. ........ 73/23.39 |
| 6,023,540 | A | | 2/2000 | Walt et al. ..................... 385/12 |
| 6,025,129 | A | * | 2/2000 | Nova et al. ..................... 435/6 |
| 6,251,865 | B1 | * | 6/2001 | Clark et al. ................... 514/15 |

* cited by examiner

Primary Examiner—Jeffrey R. Snay
(74) Attorney, Agent, or Firm—Jenkens & Gilchrist, P.C.

(57) ABSTRACT

A molecular sieve particle-based analytic chemistry system is disclosed in which populations of encoded molecular sieve particles carrying different chemical functionalities are distributed into wells etched in an optical fiber bundle. The chemical functionalities are encoded on separate shaped molecular sieve particles using luminescent dyes and/or molecular sieve particle shapes and thus, a single sensor array may carry thousands of chemistries. Such encoded molecular sieve particles can provide at least a five-fold enhancement in tunable parameters for increasing the encoding possibilities of high throughput screening assays relative to the present dye-modified polymeric microsphere standard.

77 Claims, 9 Drawing Sheets

Molecular Sieve-based Fiber-Optic Microwell Array Sensor

Step 1

Gyroid-Shaped
Molecular Sieve

Dye-Modified
Molecular Sieve

Step 2

Polished Bundle

Microwell Array

Step 3

Molecular Sieve-based Fiber-Optic Microwell Array Sensor

ENCODED MOLECULAR SIEVE PARTICLE-BASED SENSORS

CROSS REFERENCES TO RELATED APPLICATIONS

This application claims priority to U.S. Provisional Application Ser. No. 60/269,909, filed Feb. 19, 2001 which is fully incorporated by reference herein.

BACKGROUND OF THE INVENTION

1. Technical Field of the Invention

The present invention relates to the use of encoded molecular sieve particles in an optical sensor analytical system.

2. Description of the Prior Art

The use of optical fibers and optical fiber strands in combination with light absorbing dyes for chemical analytical determinations has undergone rapid development, particularly within the last two decades. Many of the recent improvements employing optical fiber sensors in both qualitative and quantitative analytical determinations concern the desirability of depositing and/or immobilizing various light absorbing dyes at the distal end of the optical fiber. In this manner, a variety of different optical fiber chemical sensors and methods have been reported for specific analytical determinations and applications such as pH measurement, oxygen detection, and carbon dioxide analyses.

Fiber optic sensors have been constructed that permit the use of multiple dyes with a single, discrete fiber optic bundle. U.S. Pat. Nos. 5,244,636 and 5,250,264 to Walt et al. disclose systems for affixing multiple, different dyes on the distal end of the bundle, the teachings of each of these patents being incorporated herein by this reference. The innovation of these patents is the placement of multiple chemical functionalities at the end of a single optical fiber bundle sensor. This configuration yields an analytic chemistry sensor that can be remotely monitored via the typically small bundle. The drawback, however, is the difficulty in applying the various chemistries associated with the chemical functionalities at the sensor's end; and, the functionalities are built on the sensor's end in a serial fashion. Not only is this a slow process, but in practice, only tens of functionalities can be applied.

U.S. Pat. No. 6,023,540 by Walt et al. discloses a microsphere-based analytic chemistry system and method for making the same is disclosed in which microspheres or particles carrying bioactive agents are combined randomly or in ordered fashion and dispersed on a substrate to form an array while maintaining the ability to identify the location of bioactive agents and particles within the array using an optically interrogatable, optical signature encoding scheme. As a preferred embodiment, U.S. Pat. No. 6,023,540 teaches the use of a modified fiber optic bundle or array as a substrate to produce a high density array. The disclosed system and method have utility for detecting target analytes and screening large libraries of bioactive agents. The teachings of U.S. Pat. No. 6,023,540 are fully incorporated by reference herein.

In brief, the main limitation to present state-of-the-art technology whether it be through the use of microspheres, microbeads or particles, is the limited number of methods available to encode the array. Currently, polymeric-based microbeads are encoded by immobilized luminescent dyes only. In addition, there is a physical limitation to how many ultraviolet, visible, and near-infrared dyes can be used simultaneously to encode an array since the emission spectra of luminescence dyes are broad. Furthermore, present state-of-the-art technology utilizes only spherical microbeads. While an optional encoding avenue would be the use of microbeads with different diameters, this approach is limited by the difficulty in fabricating a large-scale batch of microbeads with a tight and uniform bead diameter distribution (which is the only way a plurality of spherical microbeads with different diameters could be employed in a reliable optical size-encoding scheme). In other words, present state-of-the-art microparticle-based analytical systems focus on the microparticle's chemical functionality and luminescent signature only. Therefore, while a small variety of silica-based and polymeric microspheres materials have been utilized, none of these microspheres offer size and shape selectivity.

The present invention represents an improvement over U.S. Pat. No. 6,023,540 as well as other comparable flow cytometric and fiber-optic sensor systems using microbeads, microspheres and/or microparticles. The key feature of the improvement is the added analytical performance features provided by shaped molecular sieve particles, namely optical encoding based on the molecular sieve particles' macroscopic geometric shapes and increased selectivity based on the molecular sieves particles' molecular-sized pore diameters i.e., pore sizes. Such encoded molecular sieve particles can provide at least a five-fold enhancement in tunable parameters for increasing the encoding possibilities of high throughput screening assays relative to the present dye-modified polymeric microsphere, microbead or microparticle standards.

SUMMARY OF THE INVENTION

It is an object of the present invention to provide a molecular sieve particle-based fiber-optic microwell array sensor, wherein a microwell array is etched onto an optical fiber bundle that is filled with molecular sieve particles having specific morphologies and pore sizes. The molecular sieve particles can be further modified with guest molecules including but not limited to, dyes, peptides, proteins, enzymes, antigens, antibodies, receptors, ligands, catalysts, nucleic acids, and oligonucleotides to form the basis of an optical chemical sensor or biosensor. These molecular sieve particle-based fiber-optic microwell array sensors also form the basis for combinatorial encoding and/or analysis. It is another object of the present invention to provide methods for synthesizing said molecular sieve particle-based fiber-optic microwell array sensors.

A key feature of the invention is the added analytical performance features provided to the microwell sensors by the shaped molecular sieve particles—namely optical encoding based on the molecular sieve particles' macroscopic geometric shapes and increased selectivity based on the molecular sieves particles' molecular-sized pore diameters. The term "shaped molecular sieve particles" as used herein encompasses the macroscopic geometric shapes of the particles as well as their molecular-sized pore diameters. In addition to the ability to control and tune molecular sieve particle porosity, molecular sieve particles can be molecularly imprinted to further enhance selectivity to include the detection of analytes such as chiral/optically active molecules.

One key feature of the encoded molecular sieve particle-based optical sensor analytical system is the added optical encoding possibilities resulting from the plurality of the molecular sieve particle macroscopic geometric shapes that can be synthesized. In addition to spheres, molecular sieve particles can be synthesized with distinct gyroidal, discoidal, and hexagonal cylindrical shapes to increase the parameters by which optical shape-based encoding can be performed. Furthermore, the high surface area of the shaped molecular sieve particles enables encoding and detection in single microwells that is not possible with plastic beads or amphorous silica.

Perhaps the most intriguing aspect of the molecular sieve particle-based fiber-optic microwell array sensor approach is the differences in the atomic compositions of molecular sieve materials in comparison to silica-based and polymeric microsphere materials. Specifically, silica-based and polymeric microspheres materials are comprised mainly of low atomic weight atoms such as carbon, hydrogen, nitrogen, oxygen, and silicon. Conversely, molecular sieve materials can be synthesized with a variety of atoms such as aluminum, titanium, iron, nickel, cobalt, germanium, gallium, boron, tin, selenium and other metals, metalloids, and non-metals. A variety of atoms can permit a number of new and alternative methods to be utilized for array encoding such as optical encoding by spectroscopic absorption techniques and/or energy dispersive and wavelength dispersive x-ray fluorescence techniques. Such approaches have the advantage of allowing the same limited number of luminescent dyes and the same number of macroscopic geometric shapes to be used multiple times, and thus, the total possible number of encoding combinations could be increased substantially.

One embodiment of the invention provides a chemical analysis method, comprising preparing separate subpopulations of shaped molecular sieve particles, each subpopulation carrying chemical functionalities that change optical signatures of said shaped molecular sieve particles in the presence of targeted analytes;
encoding optical signature of the shaped molecular sieve particles in each subpopulation with a description of the chemical functionalities carried by that subpopulation;
combining the subpopulations to produce a system;
applying the system;
detecting changes in the optical signatures indicative of the presence of the targeted analytes; and
decoding the optical signature of the shaped molecular sieve particles to identify the chemical functionalities.

Another embodiment of the invention provides an analytic chemistry sensor, comprising:

a bundle of optical fibers; and
a population of shaped molecular sieve particles carrying chemical functionalities at a terminal end of the fiber optic bundle. The terminal end may be the distal end or the proximal end of the optic fiber bundle.

Another embodiment of the invention provides the analytic chemistry sensor further comprising a source of electromagnetic radiation for exciting optically interrogatable chemicals bound to the chemical functionalities or for exciting optically interrogatable atoms that comprise the shaped molecular sieve particle.

An embodiment of the invention provides a method for constructing and using an analytic chemistry sensor, comprising:

forming wells at terminal ends of optical fibers within a bundle;
distributing shaped molecular sieve particles carrying chemical functionalities within the wells; and;
monitoring a status of the chemical functionalities from an end face of the bundle.

A Another embodiment of the invention provides a method for constructing and using an analytic chemistry sensor, comprising:

forming wells at terminal ends of optical fibers within a bundle;
distributing shaped molecular sieve particles carrying chemical functionalities within the wells; and;
monitoring a status of the chemical functionalities from a proximal end of the bundle.

Another embodiment of the invention provides a composition comprising a plurality of optical fibers in an optical fiber array and a population of shaped molecular sieve particles, wherein said optical fibers have wells at a first terminal end of said fibers and a plurality of said wells contain at least one shaped molecular sieve particle.

Yet another embodiment of the invention provides a method of determining the presence of a target analyte in a sample comprising:
a) contacting said sample with a composition comprising:
   i) a substrate;
   ii) a population of shaped molecular sieve particles comprising separate subpopulations, each subpopulation comprising:
      1) a chemical functionality for testing for interaction with a target analyte; and
      2) an encoding optical signature that can be used to identify said chemical functionality;
   wherein said shaped molecular sieve particles are distributed on said substrate; and
b) determining the presence or absence of the target analyte.

An embodiment of the invention also provides a method of making a composition comprising:
a) forming wells at a terminal end of an optical fiber array; and
b) distributing shaped molecular sieve particles within said wells, wherein said shaped molecular sieve particles comprise separate subpopulations, each subpopulation comprising:
   i) a chemical functionality for testing for interaction with a target analyte; and
   ii) an encoding optical signature that can be used to identify said chemical functionality.

An embodiment of the invention further provides a sensor comprising:
a) an array of optical fibers;
b) a population of shaped molecular sieve particles comprising separate subpopulations, each subpopulation comprising:
   i) a chemical functionality for testing for interaction with a target analyte; and
   ii) an encoding optical signature that can be used to identify said chemical functionality;
wherein said shaped molecular sieve particles are distributed on a first terminal end of said array; and
c) a source of electromagnetic radiation.

An embodiment of the invention provides the optical fiber sensor further comprising a detector of electromagnetic radiation.

An embodiment of the invention provides a method for constructing and using an analytic chemistry sensor, comprising:

forming wells at terminal ends of optical fibers within a bundle;

distributing shaped molecular sieve particles carrying chemical functionalities within the wells; and;

monitoring a status of a molecular sieve particle shape from an end face of the bundle.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the invention presented herein.

DETAILED DESCRIPTION OF ILLUSTRATIVE EMBODIMENTS

Figure 1:
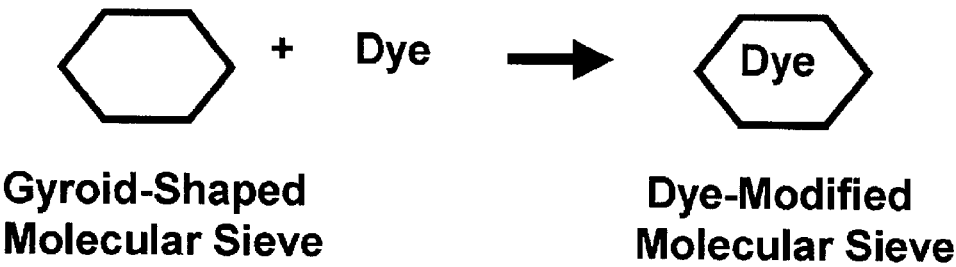
FIG. 1 shows a schematic representation of the molecular sieve particle-based fiber-optic microwell array sensor fabrication process. In Step 1 molecular sieve particles are filled with luminescent dye; in step 2, a polished fiber-optic bundle is etched to create a microwell array; and in step 3, dye-modified molecular sieve particles are deposited across the microwell array's distal face.
Figure 1:
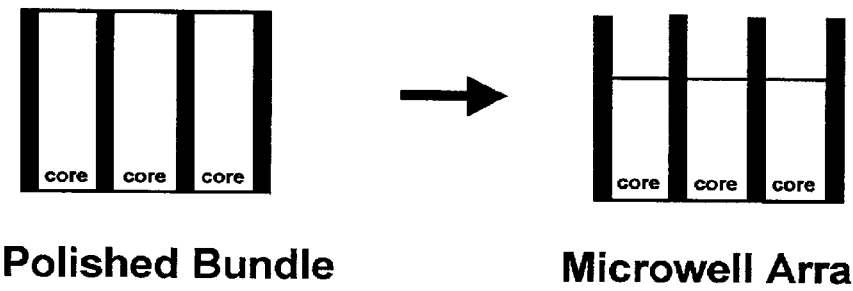
Figure 1:
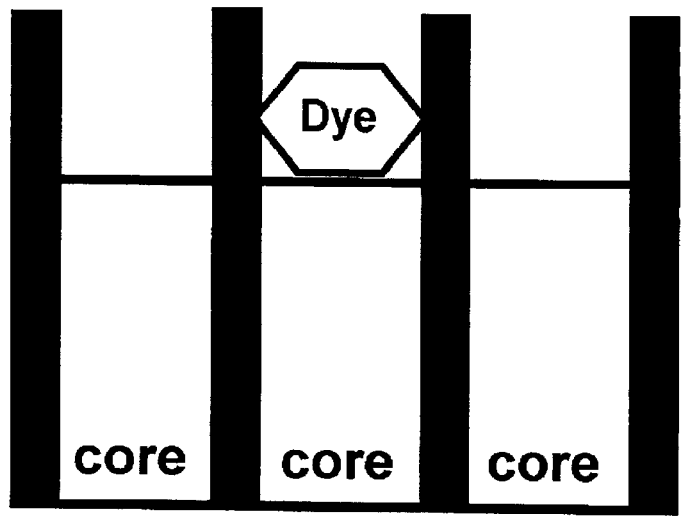

The present invention is generally concerned with molecular sieve particle-based fiber-optic microwell arrays, methods for synthesizing said arrays and practical applications of the same. The molecular sieve particle-based fiber-optic microwell arrays of the present invention can be efficacious in high throughput screening and combinatorial chemistry-related applications. The ability of shaped molecular sieve particles to provide additional selectivity to the sensor, makes the sensor a powerful tool in combinatorial encoding and/or analytical applications.

In general, according to one aspect, the invention concerns an analytic chemistry system that comprises a population of shaped molecular sieve particles. Within the population may be separate subpopulations, each of which carries a chemical functionality which changes the optical signature of the shaped molecular sieve particles in the presence of targeted analytes. This signature change can occur via many different mechanisms. A few examples include the binding of a dye-tagged analyte to the shaped molecular sieve particle, the production of a dye species on or near the shaped molecular sieve particle, the destruction of an existing dye species, a change in optical signal upon analyte interaction with dye within the shaped molecular sieve particle, or any other optically interrogatable event. Although the subpopulations may be randomly mixed together, the chemical functionality associated with each shaped molecular sieve particle is determined via an optical signature which is encoded with a description of the chemical functionality. As a result, by observing whether the optical signature of a particular shaped molecular sieve particle is exhibiting a change, or not, and then decoding the signature for the functionality of the shaped molecular sieve particle, the presence or absence of the analyte targeted by the functionality may be determined. Examples of chemical functionalities associated with molecular sieve particles include, but are not limited to, nucleic acids, oligonucleotides, peptides, proteins, enzymes, antigens, antibodies, receptors, ligands, luminophores, fluorophores, chromophores, phosphors, pH indicators, cation indicators, anion indicators, metal ion indicators, reactive oxygen species indicators, nitric oxide indicators, oxygen indicators and carbon dioxide indicators. Examples of target analytes include, but are not limited to nucleic acids, oligonucleotides, peptides, proteins, enzymes, antigens, antibodies, receptors, ligands, luminophores, fluorophores, chromophores, phosphors, acids, bases, cations, anions, metal ions, reactive oxygen species, nitric oxide, oxygen and carbon dioxide.

In specific embodiments, the shaped molecular sieve particles are encoded using dyes that are preferably entrapped within the shaped molecular sieve particles, the chemical functionality being added on to the surfaces. The dyes may be chromophores or phosphors but are preferably fluorescent dyes, which due to their strong signals provide a good signal-to-noise ratio for decoding. The encoding may be accomplished by one or more dyes (using a variety of dye concentration ratios), and more encoding dimensions may be added in the shapes of the molecular sieve particles and pore sizes, for example.

According to another aspect, the invention also concerns an analytic chemistry fiber optic bundle sensor. This sensor has a population of molecular sieve particles carrying chemical functionalities at, on or near, a distal end of the bundle. In an embodiment of the invention, an array of microwells are etched into the distal face of an optical fiber bundle and filled with molecular sieve particles having specific morphologies and pore sizes. The ability to monitor optical signature changes associated with individual or multiple molecular sieve particles is provided by coupling those signature changes into separate optical fibers or groups of fibers of the bundle for transmission to the proximal end where analysis is performed either manually, by the user, or automatically, using image processing techniques. When the molecular sieve particles are imaged directly, determination of molecular sieve particles' macroscopic geometric shapes can be performed either manually, by the user, or automatically, using image processing techniques.

In a preferred embodiment, each one of the shaped molecular sieve particles is located within separate wells formed at terminal ends of optical fibers of the bundle. These microwells are formed by anisotropic etching of the cores of the optical fibers with respect to the cladding according to a previously detailed procedure. See Pantano and Walt, Chem. Mater. 8: 2832 (1996).

In another embodiment, the shaped molecular sieve particles include separate subpopulations, typically randomly distributed in an array across the bundle end, each subpopulation carrying a different chemical functionality and an optically interrogatable code descriptive of the chemical functionality.

In another embodiment of the invention, said shaped molecular sieve particles are further modified with guest molecules or chemical functionalities including but not limited to dyes, peptides, proteins, enzymes, antigens, antibodies, receptors, ligands, catalysts and oligonucleotides to form the basis of an optical chemical sensor or biosensor. In yet another embodiment of the present invention, the molecular sieve particle-based fiber-optic microwell array sensors form the basis for combinatorial encoding and/or analytical applications. Useful shaped molecular sieve particles used in the synthesis of the molecular sieve particle-based fiber-optic microwell array sensors of the present invention include, but are not limited to, Dallas Amorphous Material-1 (DAM-1), Mobil Composition of Matter-41 (MCM-41), and Santa Barbara-15 (SBA-15) type materials having silica and transition metal oxide compositions. DAM-1 molecular sieve particles can be synthesized in spherical, gyroidal, discoidal, and hexagonal-cylindrical shapes with pore diameters of ~60 angstroms, SBA-15 molecular sieve particles can be synthesized in spherical shapes with pore diameters of ~100 angstroms, and MCM-41 has been prepared as hexagons, spheres, discoids, gyroids, tubules, rods, and helicoids with pore diameters of ~40 angstroms.

In an embodiment of the invention, fabrication of the molecular sieve particle-based fiber-optic microwell array sensors is accomplished by distribution of the shaped molecular sieve particles within the microwells, which can be accomplished in a variety of ways. For example, in particular embodiments of the invention, adsorption or sedimentation methods are used to distribute the shaped molecular sieve particles within the microwells followed by heating steps to improve retention in microwells. Such heating treatments are not practical with plastic beads. For example, in particular embodiments of the invention, the host and/or guest surfaces of the molecular sieve particle are chemically modified to improve retention in microwells. In particular embodiments of the invention, the microwell interior is chemically modified to improve molecular sieve particle retention in microwells. In another embodiment, molecular sieve particles can be grown in situ in the microwells. In all cases, the retention of the molecular sieve particle in the well is an improvement over the prior art where microbead retention in the well relies upon microbead swelling, or electrostatic attractions, or the deposition of a thin polymeric film across the bead array. The array of dye-modified molecular sieve particles are optically addressed entirely or individually by an epifluorescence microscopy/charge coupled device (CCD) imaging system, and/or a scanning electron microscope, and/or energy dispersive or wavelength dispersive X-ray fluorescence analyzer, and/or other spectroscopic imaging systems known in the art.

Although each sensor is different insofar that it has a different distribution of the subpopulations of molecular sieve particles within its wells, only those shaped molecular sieve particles that exhibit a positive optical response or signature change need to be decoded. Therefore, the burden is placed on the analysis rather than on sensor manufacture. Moreover, since the molecular sieve particles and fibers in the array can be monodisperse, the luminescent regions arising from signal generation are extremely uniform and can be analyzed automatically using commercially available microscopy analysis software, such image processing software is capable of defining different spectral regions automatically and counting the number of segments within each region in several seconds.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

WORKING EXAMPLES

In an embodiment of the invention, the molecular sieve particle-based fiber-optic microwell array sensor of the present invention is fabricated by a three step process as illustrated in FIG. 1. First, molecular sieve particles are synthesized, the excess templating molecules used in the synthesis of the molecular sieve particles are removed, and pH-sensitive fluorescent dye (fluorescein isothiocyanate; FITC) is entrapped in the sieves' pores, as described in Step 1 of FIG. 1. A fiber-optic bundle is polished and its distal face reacted in a hydrofluoric acid etching solution to create a microwell array as described in Step 2 of FIG. 1. Finally, the dye-modified molecular sieve particles are suspended in water and dispensed onto the distal face of the microwell array to create a molecular sieve particle-based fiber-optic microwell array sensor as described in Step 3 of FIG. 1.

The molecular sieve particles used in the fabrication of the present invention are prepared according to published procedures. The synthesis and characterization of Dallas Amorphous Material-1 (DAM-1) molecular sieve particles is described in "Preparation of DAM-1 Materials" by Balkus, Jr., K. J., Ma, Y., and Coutinho, D. H. published in Mater. Res. Soc. Symp. Proc, 2001, 662, NN65. SBA-15 and MCM-41 are prepared according to published procedures. See Zhao et. al., Science, 279: 548 (1998) and Kresge et. al., Nature, 359: 710 (1992) respectively. The molecular sieve particles are calcinated to remove the excess template used in their synthesis. Fluorescein isothiocyanate (FITC) is incorporated into the molecular sieve particles by soaking the particles in FITC for 1 h as described in Step 1 of FIG. 1. The FITC-modified molecular sieve particles are filtered and washed extensively with water before further processing.

The fabrication of a microwell array is carried out on an optical imaging fiber's distal face, as described in Step 2 of FIG. 1. A high-resolution imaging fiber (i.e., a coherent fiber-optic bundle) comprises thousands of micrometer-sized, coherently-fused optical fibers. A differential core/clad etching rate leads to microwell formation. For a given core diameter, microwell volume is controlled by the etch reaction time which in turn controls microwell depth. There are several methods to control the diameters of cores. One method utilizes a standard glass pipette puller to taper the imaging fiber before the etching step. Standard pullers are suitable for soft-glass imaging fibers while laser-based pipette pullers are required for all-silica imaging fibers. A second approach takes advantage of the large variety of core shapes and diameters of commercially available imaging fibers. This flexibility provides a method to tailor the size of individual microwells to accommodate a variety of different sized molecular sieve particles. The imaging fiber used is preferably a high-resolution 3.2-mm diameter imaging fiber from Edmund Scientific. This inexpensive ~50000 count bundle comprises ~8 micron wide hexagonal cores.

Microwell array preparation is carried out by cleaving (90° scribing angle) a desired length of imaging fiber with a sapphire scribe or a fine metal file. The roughly cleaved imaging fiber faces are polished by hand with 320- and 600-grit sandpaper. The imaging fiber was secured in an appropriate fiber chuck and both faces are polished successively on lapping films of 12-, 3-, and 1-micron abrasive sizes. Polishing is accomplished by maneuvering a secured fiber's face in a figure eight-like fashion over each wetted abrasive surface. Imaging fiber faces were sonicated in water between each successive film to remove fiber and abrasive particulates. All polished imaging fiber faces are inspected under a stereo-zoom microscope for scratches.

The polished distal imaging fiber face is suspended in the hydrogen fluoride (HF)-etching solution for 1–4 min as described in Step 2 of FIG. 1. The HF-etching solution (15% ammonium bifluoride ($NH_4F$:HF)) is prepared by mixing 2.5 parts (v/v) of a 40% aqueous $NH_4F$ solution, 1.2 parts (v/v) of a 49% aqueous HF solution, and 1.0 part (v/v) deionized water. This 33% (w/w) $NH_4F$:HF solution is diluted with deionized water to produce a 15% (w/w) $NH_4F$:HF solution. The fiber is removed from the HF-etching solution and quickly quenched in deionized water. The fiber is sonicated in methanol for 1–4 min where the sonication intensity is regulated to ~70% full power using a variable autotransformer. The exact sonication time is determined by periodic visual inspection of the microwell array; sonication is stopped after the microwells were clear of glass salts and core residuals. This procedure yields flat bottom wells with the same ~8-micron side-to-side dimensions as the original cores; the efficiency of the well formation across the distal imaging fiber face is ~99%. The core etch rate is ~1.15 microns/min and well depths of 1–14 microns can be obtained by varying the etch time.

Figure 2:
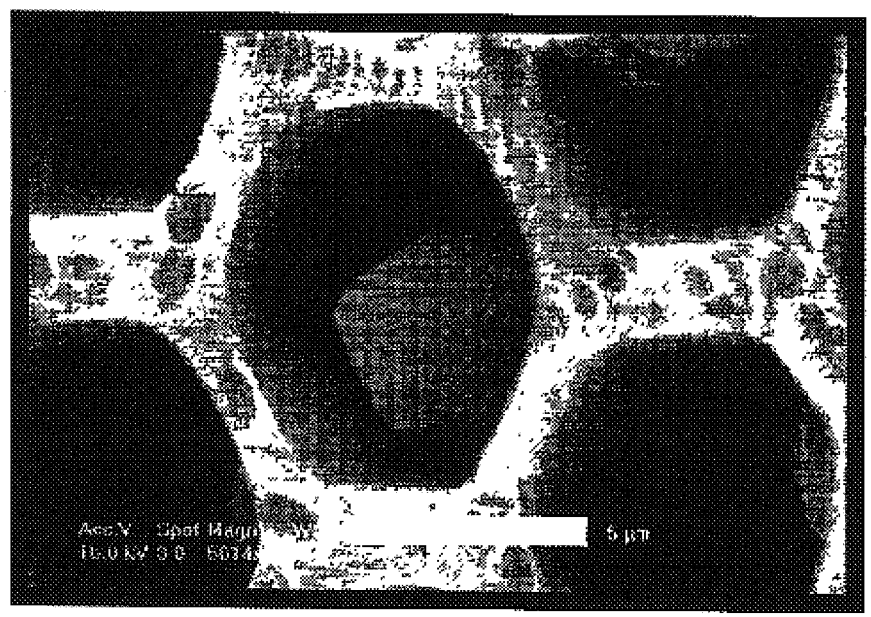
FIG. 2 shows a scanning electron micrograph of a gyroid-shaped DAM-1 molecular sieve particle in an individual microwell. The white bar denotes 5 micrometers.
Figure 3:
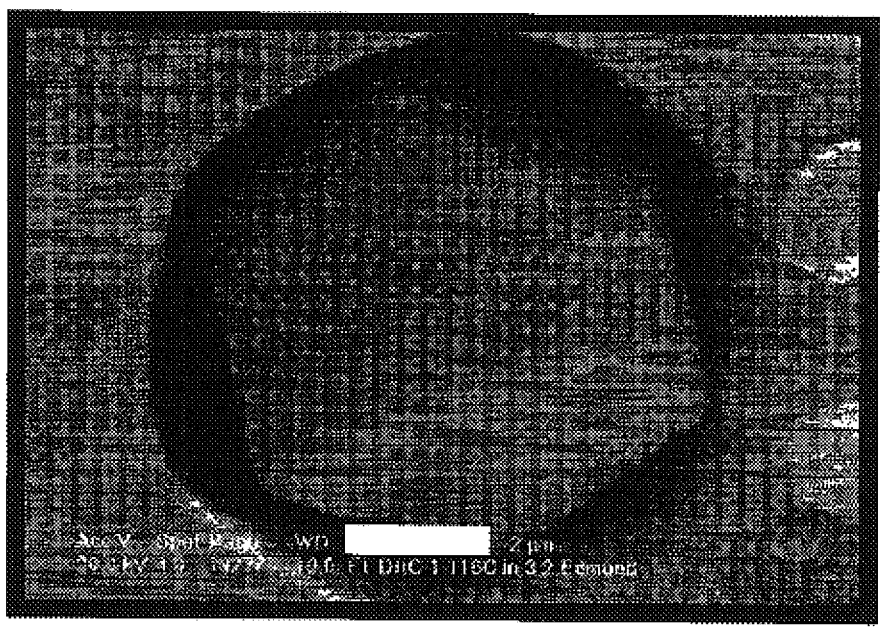
FIG. 3 shows a scanning electron micrograph of a hexagonal-cylinder shaped DAM-1 molecular sieve particle in an individual microwell. The white bar denotes 2 micrometers.
Figure 4:
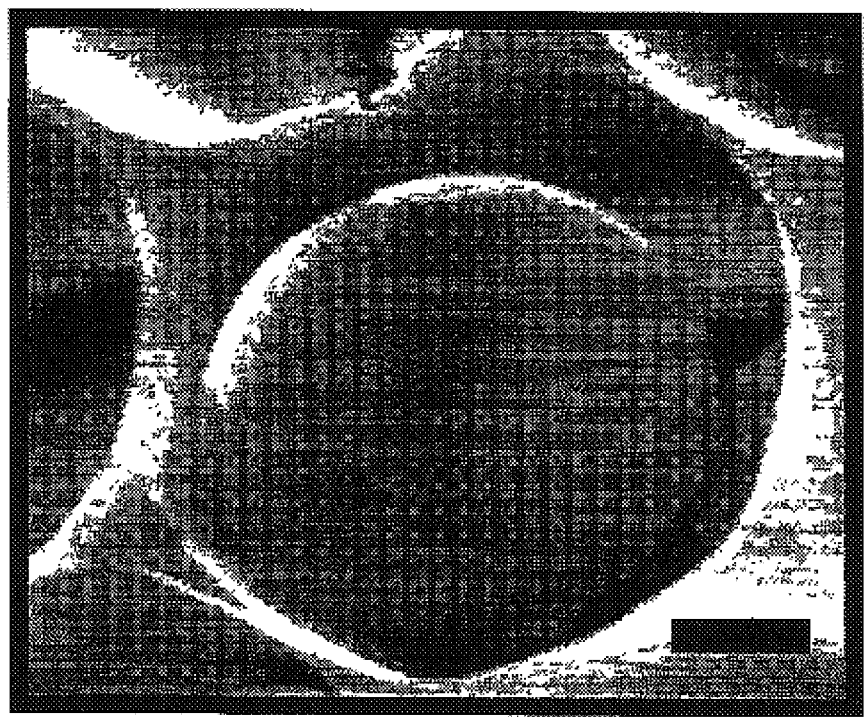
FIG. 4 shows a scanning electron micrograph of a spherical-shaped SBA-15 molecular sieve particle in an individual microwell. The black bar denotes 2 micrometers.

A 10 microliter-aliquot of a thoroughly-mixed 2.5% (v/v) aqueous solution of FITC-modified molecular sieve particles is dispersed onto a vertically-positioned microwell array face. The particle-covered array is allowed to stand for 30 min and excess particles are removed by deionized water rinsing. Scanning electron microscopy is utilized to characterize molecular sieve particle-based fiber-optic microwell array sensors. Scanning electron microscopy is preferably performed at <20 keV. Samples are sputter coated with a ~20 nm thick gold layer. FIG. 2 shows a gyroid-shaped DAM-1 molecular sieve particle in an individual microwell. FIG. 3 shows a hexagonal-cylinder shaped DAM-1 molecular sieve particle in an individual microwell. FIG. 4 shows a spherical-shaped SBA-15 molecular sieve particle in an individual microwell.

Figure 5:
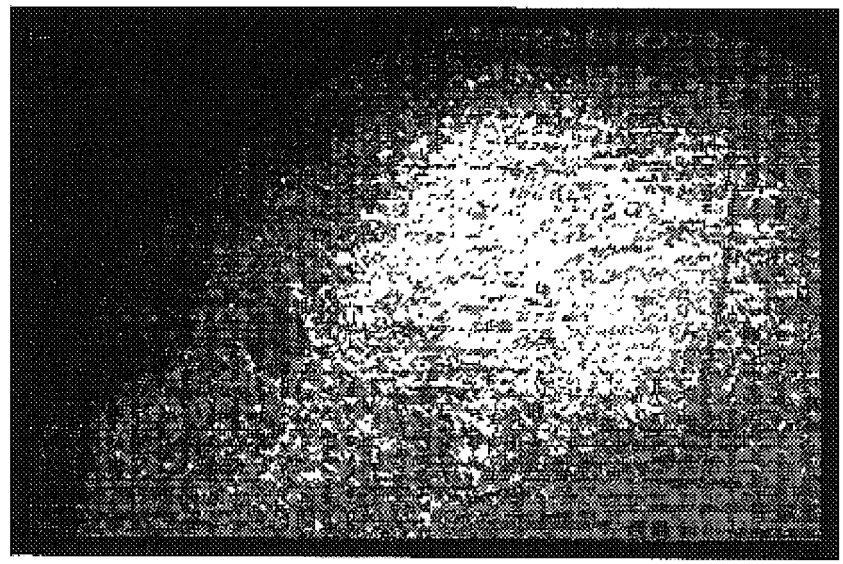
FIG. 5 represents a fluorescence image (4x) of the distal face of a DAM-1 molecular sieve particle-based fiber-optic microwell array sensor immersed in pH 8.5 phosphate buffer solution; white represents high intensities.

A modified epifluorescence microscope system (Labophot 1A; Nikon) is used for white-light and luminescence imaging with the proximal polished face of the fiber-optic bundle mounted to the microscope stage and the etched face of the fiber-optic bundle (i.e., the microwell array face) immersed in buffer. White-light and luminescence imaging can also be performed with the microwell array face mounted to the microscope stage to optically determine molecular sieve particle shapes. Phosphate buffer solutions (PBSs; pH 4.5–8.5) were prepared by mixing appropriate proportions of a 5 mM dibasic sodium phosphate/100 mM KCl solution with a 5 mM monobasic sodium phosphate/100 mM KCl solution. The collimated radiation from a 75-W xenon-arc lamp was passed through two neutral density filters (ND2+ND4) to control the excitation intensity. The radiation was passed through a 485 nm excitation filter, reflected by the 505 nm dichroic mirror, and focused on the imaging fiber's proximal face by a 4× or a 40× microscope objective. The light is transmitted through the imaging fiber to the distal imaging fiber face (i.e., the microwell array face) where it excites the FITC-modified molecular sieve particles. The fluorescence is collected by the same imaging fiber and microscope objective, transmitted through the same dichroic mirror, and filtered by a 535 nm emission filter. The filtered fluorescence image was captured by a scientific-grade CCD camera. Imaging software and a Pentium PC were used to control CCD functions and to process all images. FIG. 5 shows a representative fluorescence image (4×) of a DAM-1 molecular sieve particle-based fiber-optic microwell array sensor (3.2-mm diameter) immersed in pH 8.5 PBS.

Figure 6:
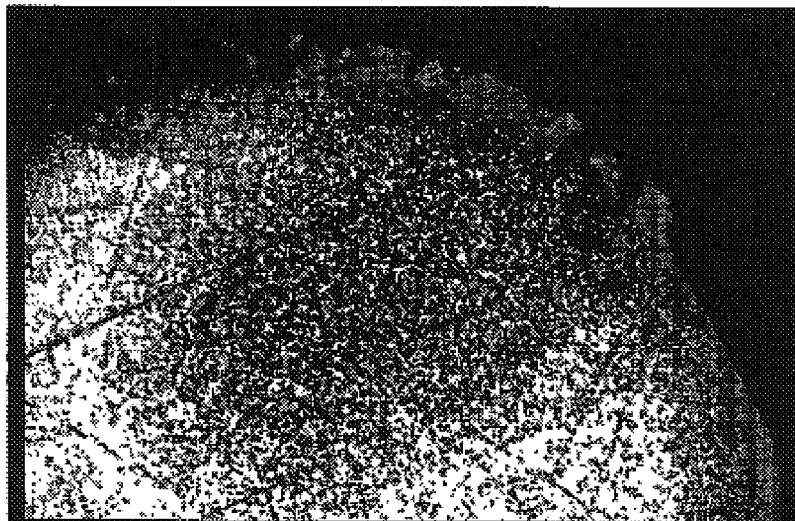
FIG. 6 represents (A) white light and (B) fluorescence images (4x) of the same distal face region of a DAM-1 molecular sieve particle-based fiber-optic microwell array sensor immersed in pH 8.5 phosphate buffer solution; white represents high intensities.
Figure 6:
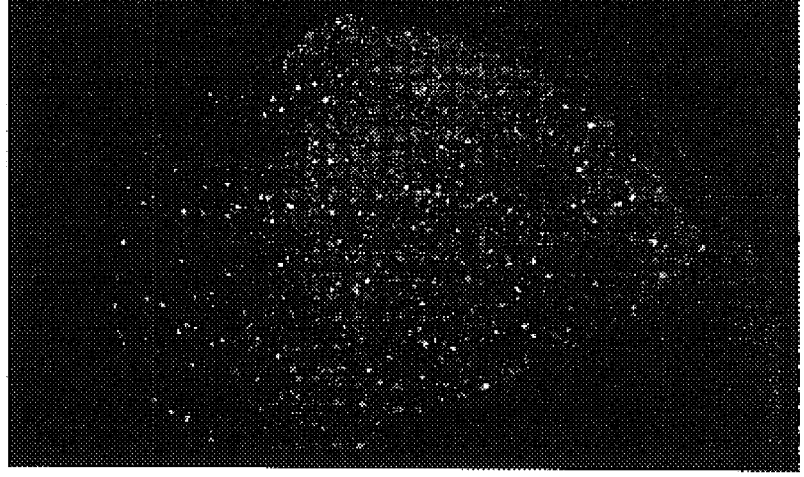

An experiment was performed to confirm that the observed fluorescence from the molecular sieve particle-based fiber-optic microwell array sensor emanated from a FITC-modified molecular sieve particle. First, the 10 microliter-aliquot of a thoroughly-mixed 2.5% (v/v) aqueous solution of FITC-modified DAM-1 particles is dispersed onto a small portion of vertically-positioned microwell array face. FIG. 6 shows a transmitted white light image (4×) and a fluorescence image (4×) of the same DAM-1 molecular sieve particle-based fiber-optic microwell array sensor immersed in pH 8.5 PBS. Both images show that DAM-1 molecular sieve particles are distributed across a well-defined region of the microwell array face. For example, dark intensities in the white-light image (FIG. 6A) indicate that some microwells were filled/partially-filled with particles such that the white light projected onto the distal array face could not be transmitted through those microwells and be detected by the CCD camera. Similarly, the bright intensities in the fluorescence image (FIG. 6B) indicate that some microwells were filled/partially-filled with dye-modified molecular sieve particles whose fluorescence could be collected in an 'epi' microscopic fashion through the bundle and detected by the CCD camera.

Figure 7:
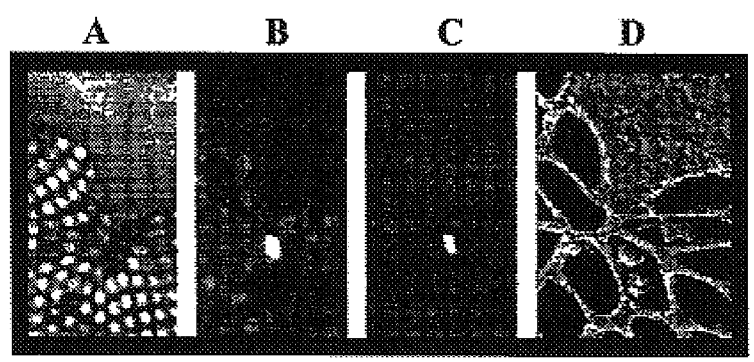
FIG. 7 represents images of the same distal face region of a DAM-1 molecular sieve particle-based fiber-optic microwell array sensor: (A) White light image (4x); (B) Fluorescence image (4x) with the sensor immersed in pH 8.5 phosphate buffer solution; (C) Fluorescence image (4x) with the sensor immersed in pH 4.5 phosphate buffer solution; (D) Scanning electron micrograph. The fluorescence images in (B) and (C) were normalized to have the same grayscale; white represents high intensities.
Figure 8:
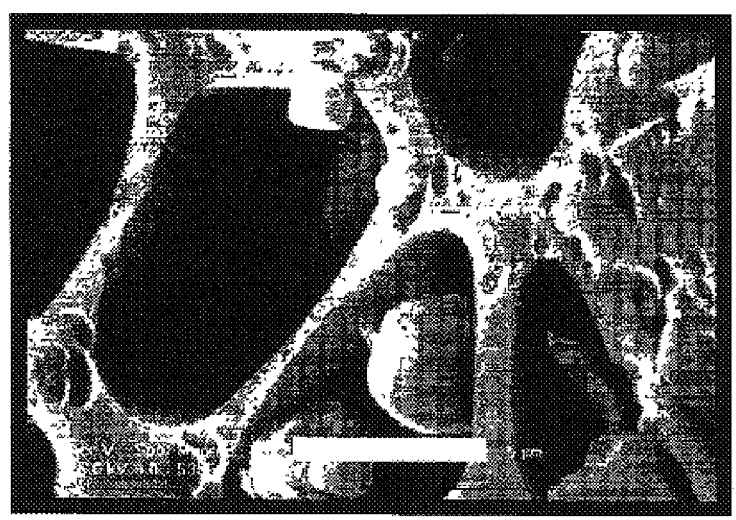
FIG. 8 shows a scanning electron micrograph of the same DAM-1 molecular sieve particle-based fiber-optic microwell array sensor as shown in FIG. 7(D). The white bar denotes 5 micrometers.

The next stage of this experiment was to acquire white-light and fluorescence images of a defect on the microwell array face so that this defect could be used for identifying the exact location of a specific dye-modified molecular sieve particle. FIG. 7A shows the white-light image of such a defect (i.e., a triangular point) on the perimeter of the microwell array face. Analysis of this image demonstrates that there are both bright regions (empty microwells) and dark regions (filled or partially-filled microwells). Fluorescence images of this region were acquired with the DAM-1 molecular sieve particle-based fiber-optic microwell array sensor immersed in pH 8.5 (FIG. 7B) and pH 4.5 (FIG. 7C) PBS. These two fluorescence images were normalized to the same grey scale and indicate that only one microwell displayed fluorescence that followed the expected behavior of the FITC pH-sensitive dye. Quantitatively, the fluorescence intensity from this microwell decreased by greater than 40% when the sensor was removed from the pH 8.5 PBS (FIG. 7B) and then immersed in the pH 4.5 PBS (FIG. 7C). It should also be noted that this microwell displayed dark intensities during white-light imaging (FIG. 7A) which further supports that it was host to a molecular sieve particle. Once the fluorescence images of this sensor region were acquired, scanning electron microscopy was used to find and identify the microwell that housed this particular molecular sieve particle. FIG. 7D shows this same sensor region and the individual microwell from which the fluorescence was generated. A higher magnification scanning electron micrograph (FIG. 8) shows that this particular microwell was filled with a gyroid-shaped DAM-1 molecular sieve particle.

PROPHETIC EXAMPLES

A photodeposition protocol has been developed that can partially fill individual microwells with a chemical sensing (polymer+dye) layer resulting in the fabrication of a microwell array chemical sensor (MWACS). MWACSs fabrication has been demonstrated using 2–14 micron-thick, water- and organic solvent-based polymer layers where individual microwell are <16 micron deep; specifically $O_2$-sensitive polysiloxane- and pH-sensitive polyvinyl alcohol-based MWACSs were characterized. Several novel analytical methodologies can be envisioned through the union of molecular sieve particles and MWACSs.

Figure 9:
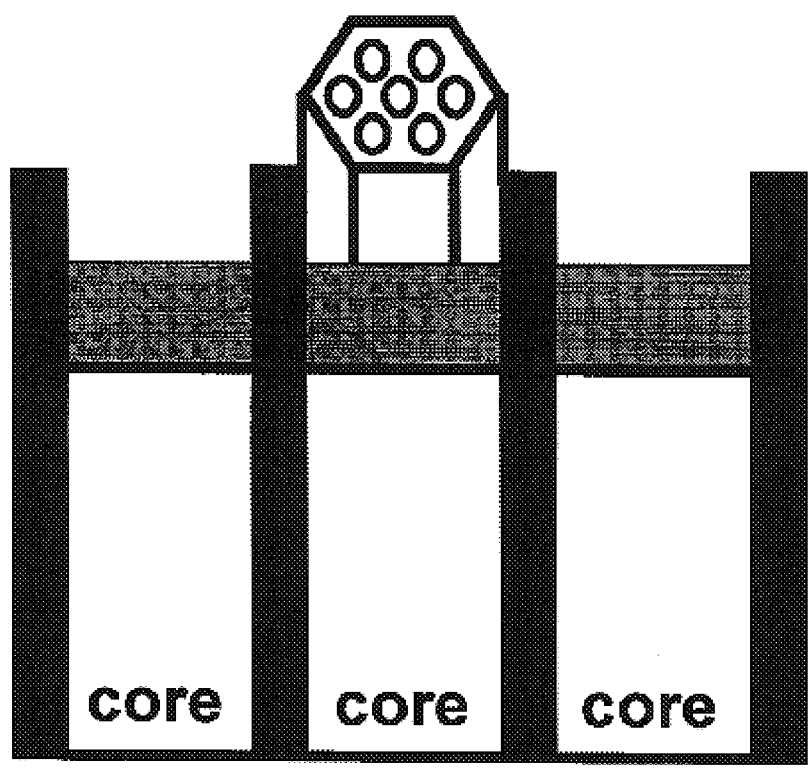
FIG. 9 represents a molecular sieve particle-based microwell array chemical sensor (MWACS) where the gray shading denotes the chemical sensing (polymer+dye) layer and the pores of the hexagonal-cylinder shaped molecular sieve particle are parallel with respect to the optical fiber/microwell's core.

The molecular sieve particle-based MWACS arrangement is depicted in FIG. 9 where the gray shading denotes the photodeposited polymeric sensing layer. In reviewing the manner by which a hexagonal-cylinder shaped DAM-1 molecular sieve particle can reside in an individual microwell (see FIG. 3), a key feature of the molecular sieve particle-based MWACS arrangement is the ability for a molecular sieve particle's pores to be aligned with the microwell's core (i.e., the optical channel).

In one embodiment, the molecular sieve particle is empty and the polymeric sensing layer contains an indicator or indicator chemistries including but not limited to, nucleic acids, oligonucleotides, peptides, proteins, enzymes, antigens, antibodies, receptors, ligands, luminophores, fluorophores, chromophores, phosphors, pH indicators, cation indicators, anion indicators, metal ion indicators, reactive oxygen species indicators, nitric oxide indicators, oxygen indicators and carbon dioxide indicators. This arrangement increases the molecular selectivity of the MWACS in that only appropriately-sized analytes will be able to diffuse through the molecular sieve particle pores and reach the polymeric chemical sensing layer.

In another embodiment, the polymeric sensing layer contains a first type of indicator chemistry and the molecular sieve particle pores contain a second type of indicator chemistry. This arrangement produces a multi-analyte sensor allowing for concurrent detection of two or more analytes. The high surface area of these molecular sieve particles provides for enhanced indicator chemistry loading and catalytic activity and thus improved analytical sensitivity relative to that of plastic beads or amphorous silica.

In another embodiment, the polymeric sensing layer contains indicator chemistry and the molecular sieve particle pores contain a drug, pharmaceutical, enzyme, protein, antibody, or oligonucleotide for controlled-release applications. It has been shown that proteins can be absorbed by molecular sieve particles and that proteins can be released from molecular sieve particles as a function of solution pH. Several novel scenarios can now be envisioned when the molecular sieve particle contained such (bio)molecules. 1) The polymeric layer can contain a pH-sensitive dye (or other indicator dye) to monitor the release process. 2) The polymeric layer can contain a photoactivatable molecule that would produce protons following irradiation in order to control the release process. 3) The polymeric layer can contain a pH-sensitive dye (or other indicator dye) to monitor the release process and a photoactivatable molecule that would produce protons to control the release process. This is possible as long as the spectral properties of the indicator and the photoactivatable molecule are properly chosen. 4) The polymeric layer can contain other photosensitive molecules (such as caged molecules or photoactivatable/photodetachable linkers) that would photochemically control the release process. Again, the high surface area of these molecular sieve particles can enable enhanced loading of the drug, pharmaceutical, enzyme, protein, antibody, or oligonucleotide in the microwell relative to that of plastic beads or amphorous silica.

What is claimed is:

1. A chemical analysis method, comprising
preparing separate subpopulations of shaped molecular sieve particles, said subpopulations carrying chemical functionalities that change optical signatures of said shaped molecular sieve particles in the presence of targeted analytes;
encoding optical signature of the shaped molecular sieve particles in each subpopulation with a description of the chemical functionalities carried by that subpopulation;
combining the subpopulations to produce a system;
applying the system;
detecting changes in the optical signatures indicative of the presence of the targeted analytes; and
decoding the optical signature of the shaped molecular sieve particles to identify the chemical functionalities.

2. The method of claim 1, wherein encoding the optical signatures with the chemical functionalities comprises doping the shaped molecular sieve particles with luminescent dyes.

3. The method of claim 1, wherein encoding the optical signatures with chemical functionalities comprises attaching encoding dyes to the shaped molecular sieve particles.

4. The method of claim 1, wherein encoding the optical signatures with chemical functionalities comprises entrapping encoding dyes within the shaped molecular sieve particles.

5. The method described in claim 1, further comprising:
encoding the shaped molecular sieve particles with the chemical functionalities by entrapping dyes within or attaching dyes to the shaped molecular sieve particles; and
applying the chemical functionalities to the shaped molecular sieve particles.

6. The method of claim 1, further comprising enabling the chemical functionalities to produce an optically interrogatable species in the presence of targeted analytes to change the optical signature.

7. The method of claim 1, further comprising changing the optical signature by the presence or absence of a luminescent signal from the shaped molecular sieve particles.

8. The method of claim 1, wherein said shaped molecular sieve particles have pore sizes ranging from 0.5 to 50 nm.

9. The method of claim 1, wherein said shaped molecular sieve shaped particles are selected from the group consisting of DAM-1, SBA-15 and MCM-41.

10. The method of claim 1, wherein said shaped molecular sieve particles have a composition comprising silicon, aluminum, and oxygen and combinations thereof.

11. An analytic chemistry sensor, comprising:
a bundle of optical fibers; and
a population of shaped molecular sieve particles carrying chemical functionalities at a terminal end of the fiber optic bundle.

12. The sensor of claim 11, wherein each of the shaped molecular sieve particles is located within separate wells formed at terminal ends of optical fibers of the bundle.

13. The sensor of claim 12, wherein the separate wells are formed by anisotropic etching of the cores of the optical fibers with respect to the cladding.

14. The sensor of claim 11, further comprising a source of electromagnetic radiation for exciting optically interrogatable chemicals bound to the chemical functionalities.

15. The sensor of claim 11, further comprising a source of electromagnetic radiation for exciting optically interrogatable atoms that comprise the shaped molecular sieve particle.

16. The sensor of claim 11, wherein the population of shaped molecular sieve particles includes separate subpopulations, each subpopulation carrying a different chemical functionality and an optically interrogatable code descriptive of the chemical functionality.

17. The sensor of claim 16, further comprising a source of electromagnetic radiation for exciting optically interrogatable chemicals bound to the chemical functionalities.

18. The sensor of claim 16, further comprising a source of electromagnetic radiation for exciting optically interrogatable atoms that comprise the shaped molecular sieve particle.

19. The sensor described in claim 16, wherein the code of each subpopulation comprises luminescent dyes.

20. The sensor described in claim 16, wherein the code of each subpopulation comprises a unique shaped molecular sieve particle.

21. The sensor described in claim 16, further comprising a filter and a frame capturing camera for detecting optical signatures indicative of a status of the chemical functionalities and optical signatures indicative of the encoding of the shaped molecular sieve particles.

22. The sensor of claim 11, wherein said shaped molecular sieve particles have pore sizes ranging from 0.5 to 50 nm.

23. The sensor of claim 11, wherein said shaped molecular sieve shaped particles are selected from the group consisting of DAM-1, SBA-15 and MCM-41.

24. The sensor of claim 11, wherein said shaped molecular sieve particles have a composition comprising silicon, aluminum, and oxygen and combinations thereof.

25. A method for constructing and using an analytic chemistry sensor, comprising:
forming wells at terminal ends of optical fibers within a bundle;
distributing shaped molecular sieve particles carrying chemical functionalities within the wells; and,
monitoring a status of the chemical functionalities from a proximal end of the bundle.

26. The method described in claim 25, wherein forming the wells comprises anisotropically etching of cores of the optical fibers with respect to cladding.

27. The method described in claim 25, further comprising forming a population of shaped molecular sieve particles in the wells from separate subpopulations, each subpopulation carrying a different chemical functionality and an optically interrogatable code descriptive of the chemical functionality.

28. The method described in claim 27, further comprising randomly distributing the subpopulations within the wells.

29. The method described in claim 27, further comprising serially adding the subpopulations to the wells.

30. The method of claim 27, wherein said shaped molecular sieve particles have pore sizes ranging from 0.5 to 50 nm.

31. The method of claim 27, wherein said shaped molecular sieve shaped particles are selected from the group consisting of DAM-1, SBA-15 and MCM-41.

32. The method of claim 27, wherein said shaped molecular sieve particles have a composition comprising silicon, aluminum, and oxygen and combinations thereof.

33. A method for constructing and using an analytic chemistry sensor, comprising:
forming wells at terminal ends of optical fibers within a bundle;
distributing shaped molecular sieve particles carrying chemical functionalities within the wells; and,
monitoring a status of a molecular sieve particle shape from an end face of the bundle.

34. A composition comprising a plurality of optical fibers in an optical fiber array and a population of shaped molecular sieve particles, wherein said optical fibers have wells at a first terminal end of said fibers and a plurality of said wells contain at least one shaped molecular sieve particle.

35. A composition comprising:
a) a substrate;
b) a population of shaped molecular sieve particles comprising separate subpopulations, each subpopulation comprising:
i) a chemical functionality for testing for interaction with a target analyte; and
ii) an encoding optical signature that can be used to identify said chemical functionality;
wherein said shaped molecular sieve particles are distributed on said substrate.

36. A composition according to claim 35 wherein said substrate is an optical fiber array comprising a plurality of individual fibers and said shaped molecular sieve particles are located within wells at a first terminal end of said fibers.

37. A composition according to claim 35 wherein said encoding optical signature comprises at least one chromophore.

38. A composition according to claim 35 wherein said encoding optical signature comprises at least one luminescent dye.

39. A composition according to claim 35 wherein said encoding optical signature comprises a unique molecular sieve particle shape.

40. A composition according to claim 38 wherein said luminescent dye is entrapped within said shaped molecular sieve particles.

41. A composition according to claim 38 wherein said luminescent dye is attached to said shaped molecular sieve particles.

42. A composition according to claim 35 wherein at least a first subpopulation of shaped molecular sieve particles is a different pore size than a second subpopulation of shaped molecular sieve particles.

43. A composition according to claim 35 wherein the individual fibers of said array are of uniform size ranging from 200 nanometers to 100 micrometers and shape including but not limited to circles and hexagons.

44. A composition according to claim 35 wherein the individual fibers of said array are of a plurality of sizes ranging from 200 nanometers to 100 micrometers.

45. A composition according to claim 35, wherein the shapes of said individual fibers are selected from the group consisting of circles and hexagons.

46. A composition according to claim 35 wherein said chemical functionality is selected from a group consisting of nucleic acids, oligonucleotides, peptides, proteins, enzymes, antigens, antibodies, receptors, ligands, luminophores, fluorophores, chromophores, phosphors, pH indicators, cation indicators, anion indicators, metal ion indicators, reactive oxygen species indicators, nitric oxide indicators, oxygen indicators and carbon dioxide indicators.

47. A composition according to claim 35 further comprising at least one target analyte interacting with at least one said chemical functionality.

48. A composition according to claim 47 wherein said target analyte is selected from a group consisting of nucleic acids, oligonucleotides, peptides, proteins, enzymes, antigens, antibodies, receptors, ligands, luminophores, fluorophores, chromophores, phosphors, pH indicators, cation indicators, anion indicators, metal ion indicators, reactive oxygen species indicators, nitric oxide indicators, oxygen indicators and carbon dioxide indicators.

49. A composition according to claim 35, wherein said shaped molecular sieve particles have pore sizes ranging from 0.5 to 50 nm.

50. A composition according to claim 35, wherein said shaped molecular sieve particles are selected from a group consisting of DAM-1, SBA-15 and MCM-41.

51. A composition according to claim 35, wherein said shaped molecular sieve particles have a composition comprising silicon, aluminum, and oxygen and combinations thereof.

52. A method of determining the presence of a target analyte in a sample comprising:
 a) contacting said sample with a composition comprising:
  i) a substrate;
  ii) a population of shaped molecular sieve particles comprising separate subpopulations, each subpopulation comprising:
   1) a chemical functionality for testing for interaction with a target analyte; and
   2) an encoding optical signature that can be used to identify said chemical functionality;
 wherein said shaped molecular sieve particles are distributed on said substrate; and
 b) determining the presence or absence of the target analyte.

53. A method according to claim 52 wherein said substrate is an optical fiber array comprising a plurality of individual fibers and said shaped molecular sieve particles are located within wells at a first terminal end of said fibers.

54. A method according to claim 52 further comprising identifying the location of each subpopulation on said substrate.

55. A method according to claim 52 further comprising identifying the shape of molecular sieve particles.

56. A method according to claim 52 wherein said encoding optical signature comprises at least one chromophore.

57. A method according to claim 52 wherein said encoding optical signature comprises at least one luminescent dye.

58. A method according to claim 52 wherein said encoding optical signature comprises a unique shaped molecular sieve particle.

59. A method according to claim 57 wherein said luminescent dye is entrapped within said shaped molecular sieve particles.

60. A method according to 57 wherein said luminescent dye is attached to said shaped molecular sieve particles.

61. A method according to claim 52 wherein at least a first subpopulation of molecular sieve particles is a different shape than a second subpopulation of molecular sieve particles.

62. A method according to claim 52, wherein said shaped molecular sieve particles have pore sizes ranging from 0.5 to 50 nm.

63. A method according to claim 52, wherein said shaped molecular sieve particles are selected from a group consisting of DAM-1, SBA-15, and MCM-41.

64. A method according to claim 52, wherein said shaped molecular sieve particles have a composition comprising silicon, aluminum, and oxygen and combinations thereof.

65. A method according to claim 53, wherein the individual fibers of said array are of uniform size ranging from 200 nanometers to 100 micrometers and shape including but not limited to circles and hexagons.

66. A method according to claim 53 wherein the individual fibers of said array are a plurality of sizes ranging from 200 nanometers to 100 micrometers.

67. A method according to claim 53 wherein the shapes of said individual fibers are selected from the group consisting of circles and hexagons.

68. A method according to claim 52 wherein said chemical functionality is selected from a group consisting of nucleic acids, oligonucleotides, peptides, proteins, enzymes, antigens, antibodies, receptors, ligands, luminophores, fluorophores, chromophores, phosphors, pH indicators, cation indicators, anion indicators, metal ion indicators, reactive oxygen species indicators, nitric oxide indicators, oxygen indicators and carbon dioxide indicators.

69. A method of making a composition comprising:
 a) forming wells at a terminal end of an optical fiber array; and
 b) distributing shaped molecular sieve particles within said wells, wherein said shaped molecular sieve particles comprise separate subpopulations, each subpopulation comprising:
  i) a chemical functionality for testing for interaction with a target analyte; and
  ii) an encoding optical signature that can be used to identify said chemical functionality.

70. A method according to claim 69 wherein said forming comprises anisotropically etching the cores of the individual fibers of said array.

71. A method according to claim 69 wherein said distributing comprises serially adding said subpopulations to said wells.

72. A method according to claim 69 wherein said distributing comprises randomly distributing said subpopulations to said wells.

73. A sensor comprising:
 a) an array of optical fibers;
 b) a population of shaped molecular sieve particles comprising separate subpopulations, each subpopulation comprising:
  i) a chemical functionality for testing for interaction with a target analyte; and
  ii) an encoding optical signature that can be used to identify said chemical functionality;
 wherein said shaped molecular sieve particles are distributed on a first terminal end of said array; and
 c) a source of electromagnetic radiation.

74. A sensor according to claim 73 further comprising a detector of electromagnetic radiation.

75. A sensor according to claim 73 wherein the shaped molecular sieve particles have pore sizes ranging from 0.5 to 50 nm.

76. A sensor according to claim 73 wherein the shaped molecular sieve particles are selected from the group consisting of DAM-1, SBA-15 and MCM-41.

77. A sensor according to claim 73, wherein said shaped molecular sieve particles have a composition comprising silicon, aluminum, and oxygen and combinations thereof.

* * * * *

UNITED STATES PATENT AND TRADEMARK OFFICE
CERTIFICATE OF CORRECTION

PATENT NO. : 6,790,672 B2
DATED : September 14, 2004
INVENTOR(S) : Kenneth J. Balkus, Jr. et al.

It is certified that error appears in the above-identified patent and that said Letters Patent is hereby corrected as shown below:

<u>Column 4,</u>
Line 5, replace "A Another embodiment" with -- Another embodiment --

Signed and Sealed this

Fourteenth Day of December, 2004

JON W. DUDAS
*Director of the United States Patent and Trademark Office*